(12) United States Patent
Hwang et al.

(10) Patent No.: US 9,345,659 B2
(45) Date of Patent: May 24, 2016

(54) USE OF MELICOPE EXTRACTS TO IMPROVE CONDITIONS CAUSED BY EXCESS LIPIDS

(71) Applicant: Avon Products, Inc., Suffern, NY (US)

(72) Inventors: Cheng S. Hwang, New Milford, NJ (US); Uma Santhanam, Tenafly, NJ (US); Jola Idkowiak Baldys, Franklin Lakes, NJ (US); John W. Lyga, Basking Ridge, NJ (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 13/808,280

(22) PCT Filed: Dec. 11, 2012

(86) PCT No.: PCT/US2012/068863
§ 371 (c)(1),
(2) Date: Jan. 4, 2013

(87) PCT Pub. No.: WO2014/092684
PCT Pub. Date: Jun. 19, 2014

(65) Prior Publication Data
US 2014/0271953 A1 Sep. 18, 2014

(51) Int. Cl.
| | |
|---|---|
| A61K 36/75 | (2006.01) |
| A61K 8/97 | (2006.01) |
| A61Q 19/00 | (2006.01) |
| A61Q 19/08 | (2006.01) |
| A61K 8/31 | (2006.01) |
| A61K 8/35 | (2006.01) |
| A61K 8/49 | (2006.01) |
| A61Q 19/02 | (2006.01) |
| A61Q 19/06 | (2006.01) |

(52) U.S. Cl.
CPC ... *A61K 8/97* (2013.01); *A61K 8/31* (2013.01); *A61K 8/35* (2013.01); *A61K 8/4973* (2013.01); *A61K 36/75* (2013.01); *A61Q 19/00* (2013.01); *A61Q 19/02* (2013.01); *A61Q 19/06* (2013.01); *A61Q 19/08* (2013.01)

(58) Field of Classification Search
None
See application file for complete search history.

(56) References Cited

U.S. PATENT DOCUMENTS

| | | |
|---|---|---|
| 5,200,429 A | 4/1993 | Sato et al. |
| 5,981,575 A | 11/1999 | Kuhajda et al. |
| 6,048,855 A | 4/2000 | De Lacharriere et al. |
| 6,103,241 A | 8/2000 | Hood |
| 7,592,024 B1 * | 9/2009 | Ptchelintsev et al. ......... 424/725 |
| 7,763,655 B2 * | 7/2010 | Kalafsky ...................... 514/566 |
| 2005/0186172 A1 | 8/2005 | Courtin |
| 2009/0301508 A1 | 12/2009 | Wang et al. |
| 2010/0048729 A1 | 2/2010 | Charveron et al. |
| 2010/0104671 A1 | 4/2010 | Ulmann et al. |
| 2010/0189821 A1 | 7/2010 | Park et al. |
| 2012/0004302 A1 | 1/2012 | Ptchelintsev et al. |
| 2012/0171314 A1 | 7/2012 | Florence |

FOREIGN PATENT DOCUMENTS

| | | |
|---|---|---|
| GB | 1532938 | 11/1978 |
| KR | 10-2007-0111635 | 11/2007 |
| WO | 02/087565 | 11/2002 |
| WO | 2004026249 A2 | 4/2004 |
| WO | 2009048282 A2 | 4/2009 |

OTHER PUBLICATIONS 2005 http://en.wikipedia.org/wiki/Melicope.*
Aja et al., Pharmacological stimulation of brain carnitine palmitoyl-transferase-1 decreases food intake and body weight, 2008, Am J Physiol Regul Integr Comp physiol, 294: R352-R361.*
deVries et al., Adi8pose tissue fatty acid composition and its relations to diet and plasma lipid concentrations in hemodialysis patients, American J. Clin Nutrition. 1991; 53:469-73.
Ntambi et al., Loss of stearoyl-CoA desaturase-1 function protects mice against adiposity, PNAS Aug. 20, 2002; 99:17 1482-1486.
U.S. Appl. No. 12/648,581, filed Dec. 29, 2009, Lyga et al.
U.S. Appl. No. 14/335,467, filed Jul. 18, 2014, Lyga et al.
U.S. Appl. No. 13/710,536, filed Dec. 11, 2012, Hwang et al.
Barrows et al., "Anti-TB activity of Evodia elleryana bark extract," Fitoterapia, vol. 78, No. 3, pp. 250-252 (2007).
Jones et al., "Essential Oils from the Queensland," Department of Chemistry, vol. 1, No. 27, pp. 1-7 (1946).
Khan et al., "Antimicrobial activity of Evodia elleryana," Fitoterapia, vol. 71, pp. 72-74 (2000).
Byers, H. Randolph; "Role of Cytoplasmic Dynein in Perinuclear Aggregation of Phagocytosed Melanosomes and Supranuclear Melanin Cap Formation in Human Keratinocytes," The Journal of Investigative Dermatology, vol. 121, No. 4, (2003).

* cited by examiner

*Primary Examiner* — Terry A McKelvey
*Assistant Examiner* — Catheryne Chen
(74) *Attorney, Agent, or Firm* — David M. Joyal; Joan M. Mcbillycuddy

(57) ABSTRACT

Methods of using extracts of *Melicope* to impart anti-lipid benefits to skin and/or improve skin conditions resulting from an over-production of lipids.

27 Claims, No Drawings

USE OF MELICOPE EXTRACTS TO IMPROVE CONDITIONS CAUSED BY EXCESS LIPIDS

CROSS-REFERENCE TO RELATED APPLICATIONS

This application claims priority benefit, under the national stage entry under 35 U.S.C. 371 of International Application No. PCT/US12/68863 filed on Dec. 11, 2012, the contents of which application are hereby incorporated by reference in their entirety. PCT application no. PCT/US12/68863 was filed concurrently with and claims priority to PCT Application Serial No. PCT/US12/68856 filed on Dec. 11, 2012; PCT Application Serial No. PCT/US12/68858 filed on Dec. 11, 2012; PCT Application Serial No. PCT/US12/68866 filed on Dec. 11, 2012; PCT Application Serial No. PCT/US12/68862 filed on Dec. 11, 2012; PCT Application Serial No. PCT/US12/68865 filed on Dec. 11, 2012; and U.S. application Ser. No. 12/710,617 filed on Dec. 11, 2012; the entirety of each of which is incorporated by reference in its entirety herein for all purposes.

FIELD OF INVENTION

The present invention relates generally to the use of cosmetic compositions which comprise *Melicope* extracts for topical application to skin in need thereof, in particular to treat, reduce, or ameliorate the excess presence or over-production of lipids and or oils. This use of a cosmetic composition comprising a *Melicope* extract provides benefits to the skin, including but not limited to, the reduction of lipid overproduction to improve the condition and appearance of the following: skin affected by excess sebum (oily skin or hair), acne-prone skin, body odor, large pores, and/or cellulite.

BACKGROUND OF THE INVENTION

Consumers are increasingly interested in cosmetics that treat, mitigate, or delay the effects of excess lipids on their skin. The signs of excess lipids manifest themselves in an unflattering oiliness and shine to the skin due to over-production of sebum, in the "orange peel" or "cottage cheese" appearance and texture of skin affected by cellulite, or in the bulges that occur with excess subcutaneous fat. There is an active interest in the cosmetics industry to develop products that may be used to reduce the amount of lipids (anti-lipids) within the skin and thereby provide anti-oil/sebum, anti-cellulite, and anti-obesity benefits.

Sebum is an oily secretion of the sebaceous glands (sebocytes) of the skin that contains lipids (fat, triglycerides, and fatty acids), keratin, and cellular materials. Sebum normally constitutes a natural moisturizer for the epidermis maintaining its integrity. The level of sebum production varies from person to person and depends largely on sex and age. In particular, sebum production is influenced by hormones, i.e. androgens such as testosterone, and therefore occurs most prevalently in males during adolescence. During the teenage years, the complexion of the skin, i.e., the color and appearance of the skin, is oily primarily due to these hormonal changes. However, in both men and women sebum production can be stimulated by physical or emotional factors which are altered by hormones. Besides age and sex factors, sebum production is also influenced by stress, use or consumption of pharmaceuticals and drugs such as muscle stimulants and/or the presence of disease states that interfere with the autonomic nervous system such as Parkinson's, strokes, etc.

Some people exhibit hyperseborrhoeic skin characterized by an exaggerated secretion and excretion of sebum. Generally, individuals with hyperseborrhoeic skin exhibit sebum levels of greater than 200 µg/cm$^2$ measured on the forehead. This overproduction of sebum may lead to aesthetic problems, such as oily/shiny skin or hair, acne-prone skin, enlarged pores, thickened skin, or poorer hold of makeup. Additionally, the excess sebum may act as a catalyst for acne by clogging pores leading to the formation of comedones ("blackheads" or "whiteheads"), which, when left untreated, may become inflamed and progress into acne vulgaris. Additionally, odors may be emitted as a result of excess sebum accumulation, production, or excretion.

Cellulite is a lumpy uneven type of skin texture caused by the excess accumulation of lipids (triglycerides and fatty acids) within adipocytes in subcutaneous tissues. Cellulite accumulates primarily on the buttocks, abdomen, thighs, and limbs of many women. It is considered unsightly because it gives the tissue underlying the skin an "orange peel" or "cottage cheese" look. Compressing the skin, as when sitting or crossing the legs, produces a "mattress appearance" with bulging and pitting of the fatty layer. Nodules of fat may be felt trapped within hardened connective tissue. The histology of cellulite-affected skin indicates that cellulite results from a combination of enlarged fat tissue and weak dermal structure and connective tissue septa. Excess fat accumulation increases the volume of adipocytes, which bulge into a weakened dermis ("bleeb") to create the characteristic irregularities in the appearance of the dermal surface. Causes of cellulite include, but are not limited to, hereditary, intestinal, circulatory, lymphatic, hormonal, and lifestyle factors.

Lipids within the body, i.e. those produced by sebocytes and adipocytes, are mediated by several pathways. However, lipid metabolism appears to be controlled by peroxisome proliferator-activated receptors ("PPARs"), which form a superfamily of nuclear transcription factors. The PPARs are ligand-dependent intracellular proteins that stimulate transcription of specific genes by binding to specific DNA sequences in the nucleus following activation by the appropriate ligands. PPAR-γ activity, in particular, is governed by the binding of small lipophilic ligands, mainly fatty acids, derived from nutrition or metabolic pathways that themselves are often controlled by PPAR-γ. PPAR-γ heterodimerizes with the retinoid X receptor (RXR), leading to transactivation of genes that encode proteins involved in adipogenesis. Among the genes transactivated are several adipogenic genes including, but not limited to, fatty acid synthase (FAS), Stearoyl-CoA desaturase-1 (SCD-I), ATP-citrate lyase (ACL), glucose-6-phosphate dehydrogenase (G6PD), malic enzyme (ME), SREBP1c, SIP, fatty aci-CoA oxidase (ACO), long and medium chain acyl-CoA dehydrogenase (LCAD and MCAD), fatty acid binding protein (FABP), fatty acid translocase (CD36), fatty acid transport protein (FATP), lipoprotein lipase (LPL), and/or alipoproteins B (ApoB). Indeed, it is believed that PPAR-γ is the centerpiece of a feed-forward pathway that favors differentiation of and energy storage by adipocytes. PPAR-γ agonists (e.g. rosiglitazone) have been shown to increase fat synthesis and storage in adipocytes; whereas lipid accumulation and adipocyte differentiation are impaired when PPAR-γ levels are reduced.

Among the genes up-regulated upon activation of PPAR-γ is FAS which encodes the enzyme FAS, necessary for the synthesis of triglycerides. FAS is one of four major enzymes involved in the fatty acid biosynthetic pathway in humans. The fatty acid biosynthetic pathway components include: acetyl-CoA carboxylase, which is the rate-limiting enzyme that synthesizes malonyl-CoA; malic enzyme, which produces NADPH; citrate lyase, which synthesizes acetyl-CoA; and FAS, which catalyzes NADPH-dependent synthesis of fatty acids from acetyl-CoA and malonyl-CoA. Inhibition of FAS interferes with fatty acid synthesis and is disclosed for example in Kuhajda, U.S. Pat. No. 5,981,575 and Orlow, et al., PCT Patent Application WO 02/087565.

SCD-I is a key lipogenic enzyme that catalyzes the synthesis of monounsaturated fatty acids. Its preferred desaturation substrates are palmitoyl-CoA and stearoyl-CoA, which are converted to palmitoleoyl-CoA and oleoyl-CoA, respectively. Oleic acid constitutes nearly half of the total fatty acids in the adipose tissue (de Vries, Am J. Clin Nutrition. 1991; 53:469-73). The absence of SCD-I leads to reduced triglyceride synthesis, decreased lipid storage, and decreased lipid export. Further, SCD-1 deficient mice have shown that loss of SCD-1 increases the expression of genes involved in fatty acid oxidation and reduces the expression of lipogenic genes. As a result of changes in gene expression, SCD-1-deficient mice have reduced body fat and increased energy expenditure and oxygen consumption (Ntambi et al. PNAS 2002; 99:1 1482-1486).

Generally, cosmetic treatments for excess lipid production provide relief from the symptoms, i.e., oiliness, enlarged pores, acne prone skin, irregular skin texture, etc., and fail to address the underlying cause. For example, the classic approach to addressing oily or shiny skin is the use of powders that provide an immediate masking effect by absorbing the excess sebum on the skin's surface. Additionally, various astringents and cleaning agents may be used to control sebum. Cellulite remedies may involve dieting to reduce fat intake, exercise to increase fat metabolism and prevent the build-up of cellulite, and massage and hydrotherapy to stimulate lymphatic drainage. However, all of these means for lipid reduction on the skin surface or within subcutaneous fat are limited, producing little sustainable visible results over extended periods of time. Astringents and cleaners may actually exacerbate the condition through a rebound effect. These means for combating sebum, cellulite, or subcutaneous fat are limited, and the need remains for additional approaches.

The *Melicope* plant genus includes about 150 different species of shrubs and trees in the family, which may be found in western Hawaii, tropical regions of Asia, Australia and New Zealand. Plants in the *Melicope* genus are commonly referred to as "Corkwood" or "Doughwood" in Australia and as "Alani" in Hawaii. We have previously shown that extracts of *Melicope* have an anti-inflammatory effect in U.S. Pat. No. 7,592,024, hereby incorporated by reference in its entirety for all purposes, and a restorative effect on the adipose septum, see U.S. patent application entitled "Use of adipose septum protein modulators and compositions thereof" filed contemporaneously with the current case and hereby incorporated by reference in its entirety for all purposes. However, prior to this invention it was not reported that *Melicope* extracts could reduce lipid accumulation and/or over-production.

There remains a need for cosmetic compositions which reduce the excess accumulation and/or over-production of lipids. It is therefore an object of the present invention to provide new compositions and methods for inhibiting excess lipid accumulation and/or over-production. It is a further object of the invention to improve the overall appearance of skin affected by excess lipids or lipid over-production, including treatment, reversal, and/or prevention of oily skin and/or hair, acne-prone skin, body odors, enlarged pores, cellulite and/or excess body fat.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, it has been found that extracts of *Melicope* are surprisingly potent regulators of lipid production within the body and thus are beneficial agents against oily complexions, cellulite, and weight gain.

One embodiment of the current invention relates to a method for providing a benefit to human skin experiencing lipid over-production by topically applying to skin in need thereof a composition comprising an effective amount of *Melicope* extract in a cosmetically acceptable vehicle for a time sufficient to achieve an improvement in the appearance of said skin. In certain embodiments, the skin may be located on a human's back, shoulders, neck, scalp, hair or face. In one embodiment, the human skin is located on the human's face.

In a further embodiment of the method, the skin benefit may be selected from the group consisting of: reducing lipid production by sebaceous glands; reducing lipid synthesis in subcutaneous adipose tissue; reducing triglyceride synthesis; reducing fatty acid synthesis; preventing and/or improving conditions related to skin associated with inhibited lipolysis; preventing and/or improving conditions related to skin associated with nonselective or partially selective PPAR-γ stimulators/up regulators; preventing and/or improving conditions related to skin associated with nonselective or partially selective up regulation of adipogeneic genes typically up regulated by PPAR-γ activation; preventing and/or improving conditions related to skin associated with nonselective or partially selective FAS stimulators/up regulators; preventing and/or improving conditions related to skin associated with nonselective or partially selective SCD-1 receptor stimulators/up regulators; preventing, ameliorating or treating oily skin; preventing, ameliorating or treating oily hair; preventing, ameliorating or treating oily scalp; preventing, ameliorating or treating enlarged pores; preventing, ameliorating, or treating acne-prone skin; preventing, ameliorating or treating body odors associated with excess sebum production; preventing, ameliorating or treating cellulite in adults; preventing, ameliorating or treating excess accumulation or production of subcutaneous fat in adults; improving skin texture associated with cellulite; and/or combinations thereof.

In certain embodiments, the skin in need thereof may be skin having excess sebum. In a further embodiment of the method for treating skin with excess sebum, the skin benefit may selected from the group consisting of: restoration of a matte finish to the skin; an evening of skin type; reduction in oily/greasy feel to skin and/or hair; reduction in the incidence of dandruff; reduction in the incidence of blocked/clogged pores; reduction in the incidence of comedones; reduction in the incidence of acne lesions; reduction in the area over expressing or over-producing lipids; reduction in thickness of skin affected by over-production of lipids; and/or combinations thereof.

In a further embodiment, the skin in need thereof is skin having cellulite, and in one embodiment the cellulite may be found on a thigh, buttock, abdomen, hip, and/or upper arm region. In certain embodiments, the skin benefit may be selected from the group consisting of: reduction in the appearance of cellulite lumpiness and/or unevenness; reduction in pitting appearance of cellulite upon squeezing; reduction in the extent of area affected by cellulite; prevention or delay in the recurrence of cellulite; improvement in adipocyte/fat tissue disposition; and/or combinations thereof.

In yet another embodiment of the current method, the skin in need thereof is skin with excess subcutaneous fat.

In a further embodiment, the *Melicope* extract may be derived from *Melicope ellyrana, Melicope hayesii*, and/or hybrids or combinations thereof. In another embodiment, the *Melicope* extract is an essential oil, and in a further embodiment the essential oil may include caryophylene, bicyclogermacrene, zierone, and evodone. In one embodiment, an effective amount of the *Melicope* extract is about 0.001% to about 25% by weight, and in a further embodiment, the *Melicope* extract is present in an amount from about 0.001% to about 1% by weight.

The *Melicope* extract may be used in combination with at least one other anti-lipid agent in certain embodiments. In one embodiment, the other anti-lipid agent may be a carnitine palmitoyl transferase-1 stimulator. In a further embodiment, the *Melicope* extract may be used in combination with at least one anti-cellulite agent. In one embodiment, the anti-cellulite agent is selected from the group of a phophodiesterase inhibitor, an adenylate cyclase activator, a lipolysis stimulator, a beta-adrenergic receptor agonist, an alpha-2-adreneric receptor antagonist, *perilla* oil, carnitine, creatine, and combinations thereof. In a further embodiment, the anti-cellulite agent may be selected from the group of a xanthine analog, forskolin, a forskohlii extract, a hawthorne extract, a cola extract, isoproterenol, yohimbine, *Ginkgo biloba* extract, *perilla* oil, and combinations thereof. In certain embodiments, the anti-cellulite agent is caffeine. In yet a further embodiment, the *Melicope* extract may be used in combination with at least one collagen and/or elastin stimulator.

In certain embodiments, the composition is a leave-on composition. In one embodiment of the current method, the composition is applied at least once daily for a period of time sufficient to improve the appearance of the skin. In another embodiment, the composition is topically applied daily for a period of at least 4 weeks.

In one embodiment, the cosmetically acceptable vehicle is a transdermal patch, and in another embodiment it is an emulsion.

These and other aspects of the present invention will be better understood by reference to the following detailed description and accompanying figures.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, and some features may be exaggerated to show details of one embodiment components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

It has been found that extracts of *Melicope* are surprisingly capable of reducing the presence and/or production of lipids. Without wishing to be bound to a particular theory, the inventors believe that *Melicope* extracts affect multiple steps of the lipid production pathway in adipocytes and this confers the extract with high potency and a unique and prolonged model of action. Further, inventors believe that the *Melicope* extracts are able to interfere with the activation of PPAR-γ and/or one or more of the adipogeneic genes up-regulated by PPAR-γ activation. The extracts may interfere with the upregulation of PPAR-γ and/or one of the adipogenic genes upregulated upon activation of PPAR-γ, and in one embodiment may interfere with the upregulation of PPAR-γ, FAS, and/or SCD-1.

In view of these findings and others, it is contemplated that the cosmetic use of compositions comprising *Melicope* extracts will be useful in combating excess lipids in or on affected skin including providing relief to people in need thereof, including those individuals suffering from, oily skin/complexion, oily hair, acne-prone skin, enlarged pores, cellulite, and/or weight gain. In a further embodiment, the compositions of the current method are not administered to skin exhibiting acne, i.e. comedones, acne vulgaris, acne cysts, etc.

The methods of the present invention provide for topical application of compositions which comprises an effective amount of a *Melicope* extract to treat, reverse, ameliorate and/or prevent signs of lipid overproduction on or within the skin. Such benefits include without limitation, the following:

1. Reduction of lipid production by sebaceous glands;
2. Reduction of lipid synthesis in subcutaneous adipose tissue;
3. Reduction of triglyceride synthesis;
4. Reduction of fatty acid synthesis;
5. Prevention and/or improvement of conditions related to skin associated with inhibited lipolysis;
6. Prevention and/or improvement of conditions related to skin associated with nonselective or partially selective PPAR-γ receptor stimulators/up regulators;
7. Prevention and/or improvement of conditions related to skin associated with nonselective or partially selective up regulation of adipogeneic genes typically up regulated by PPAR-γ activation;
8. Prevention and/or improvement of conditions related to skin associated with nonselective or partially selective FAS stimulators/up regulators;
9. Prevention and/or improvement of conditions related to skin associated with nonselective or partially selective SCD-1 stimulators/up regulators;
10. Prevention, amelioration or treatment of oily skin;
11. Prevention, amelioration or treatment of oily hair;
12. Prevention, amelioration, or treatment of oily scalp;
13. Prevention, amelioration or treatment of enlarged pores;
14. Prevention, amelioration, or treatment of acne-prone skin;
15. Prevention, amelioration, or treatment of body odors associated with excess sebum production;
16. Prevention, amelioration, or treatment of cellulite in adults;
17. Prevention, amelioration, or treatment of excess accumulation or production of subcutaneous fat in adults;
18. Improvement of skin texture associated with cellulite; or combinations thereof.

In practice, the compositions of the invention are applied to skin in need of treatment, that is, skin which suffers from a deficiency or loss in any of the foregoing attributes or which would otherwise benefit from improvement in any of the foregoing skin attributes.

In certain embodiments the compositions and methods of the invention are directed to the prevention, treatment, and/or amelioration of lipid over-production which leads to or has resulted in cellulite. Cellulite results from a combination of enlarged fat tissue and weak dermal structure and connective tissue. One of the approaches to improve the appearance of cellulite is to reduce the amount of fat/lipids in the adipocytes (fat cells). It was not expected that *Melicope* extracts could reduce lipid accumulation/production in adipocytes. The novelty of this invention is to use *Melicope* extracts to decrease excess lipid accumulation/production in any part at risk of or exhibiting cellulite. In this case, the compositions are applied to skin in need of treatment, by which is meant skin having, or at risk of developing, cellulite. In one embodiment, the compositions are applied directly to the afflicted skin. The compositions and methods are suitable for the treatment of cellulite on any surface of the skin, including without limitation, the skin of the buttocks, abdomen, thighs, and/or limbs.

In one embodiment, the composition is intended for use as a non-therapeutic treatment. In another embodiment, the composition is an article intended to be rubbed, poured, sprinkled, or sprayed on, introduced into, or otherwise applied to the human body for cleansing, beautifying, promoting attractiveness, or altering the appearance, in accordance with the US FD&C Act, sec. 201(i).

DEFINITIONS

All terms used herein are intended to have their ordinary meaning unless otherwise provided.

The term "active amount" refers to the amount of a *Melicope* extract absent diluent, solvent, carrier, filler or any other ingredient. An "amount effective" or an "effective amount" to provide a particular anti-lipid benefit to the skin refers to the "active amount" of extract required to provide a clinically measurable improvement in the particular manifestation of the lipid over-production, i.e., an unwanted feature associated with over-production of lipids, when applied or administered for a time sufficient to provide a clinically measurable improvement in the particular manifestation of lipid overproduction.

As used herein, the term "a person in need thereof" refers to an individual with a normal but noticeable and undesired skin condition, unwanted feature, due to the excess presence or over-production of lipids, e.g. hyperseborrhoea, cellulite, excess body fat, etc., or an individual that elects to decrease the presence or production of lipids in the absence of a noticeable and undesired skin condition, i.e. as a preventative or prophylactic such as for acne or cellulite.

As used herein, the term "consisting essentially of" is intended to limit the invention to the specified materials or steps and those that do not materially affect the basic and novel characteristics of the claimed invention, as understood from a reading of this specification.

By "cosmetically acceptable" it is meant that a particular component is generally regarded as safe and nontoxic at the levels employed.

As used herein, "decreasing PPAR-γ signaling" and related expressions refer to reducing the extent to which PPAR-γ can signal a sebocyte and/or adipocyte cell to produce and/or store lipids, e.g., by decreasing the expression of PPAR-γ and/or one of the adipogenic genes up regulated by the activation of PPAR-γ. It is believed that the decrease in PPAR-γ's signaling results in a perceptible reduction in the appearance of excess lipids or reduction of lipid production at an affected area. As an example, a decrease in PPAR-γ inhibition can be directly measured, e.g., by measuring a reduction in PPAR-γ gene expression, where the *Melicope* extract acts to decrease PPAR-γ gene expression and/or the expression of adipogenic genes up-regulated upon activation of PPAR-γ, and in certain embodiments the expression of FAS and/or SCD-1, within human adipocytes as measured by any means known in the art, or as described herein. In some embodiments, PPAR-γ gene expression is decreased by at least about 10%, at least about 20%, at least about 25%, at least about 30%, at least about 35%, at least about 40%, at least about 50%, or up to about 100%, compared to the level of PPAR-γ gene expression in the absence of the *Melicope* extract. In further embodiments, adipogenic gene expression, such as that of FAS and/ or SCD-1, is decreased by at least about 10%, at least about 20%, at least about 25%, at least about 30%, at least about 35%, at least about 40%, at least about 50%, or up to about 100%, compared to the level of adipogenic gene expression in the absence of the *Melicope* extract. Example 2 below illustrates a method for evaluating the reduction in expression of PPAR-γ and/or an adipogenic gene upregulated by the activation of PPAR-γ.

As used herein, the term "essential oil" refers to the volatile ethereal fraction obtained from a plant or plant part by a physical separation process such as distillation or chromatographic separation. The essential oils are typically terpenoids often comprising monoterpenes and have the odor and flavor of the plant from which they were extracted. In certain embodiments, the essential oils may include, but are not limited to, caryophylene ($C_{15}H_{24}$), bicyclogermacrene ($C_{15}H_{22}$), zierone ($C_{15}H_{22}O$), or evidone ($C_{10}H_{12}O_2$).

As used herein, the term "lipid" refers to a fatty or waxy organic compound that is readily soluble in a nonpolar solvent (e.g. ether) but not in polar solvent (e.g. water) and functions within the body to provide energy storage, homeostasis, or moisture to the skin. Lipids may include waxes, oils, sterols, monoglycerides, diglycerides, triglycerides (fats), fatty acids, and phospholipids. Further, this definition may exclude membrane lipids, such as those found in lipid bilayers. Bilayer lipids include, for example, lipids in the bilayers of the stratum corneum, or other cutaneous lipids, such as cholesterol, cholesterol esters, free fatty acids, and ceramindes that make up the lipid bilayers of skin. See, e.g., U.S. Pat. Appl. Pub. No. 2006/0110815. The terms sebum, cellulite, oils, triglycerides, fat, and fatty acids may be used herein interchangeably to refer to lipids.

As used herein, the term "*Melicope*" includes (1) *Melicope hayesii*, as described above; (2) *Melicope elleryana*, a tree that can reach heights of up to 35 meters found along creeks, swamp forests, or vineforests through Malesia and Australia; (3) hybrids of these species of *Melicope* or hydrids of at least one of these species of *Melicope* and other species of *Melicope*, which may occur naturally through cross-pollenation or through active cultivation i.e., planned cross-pollenation and/ or grafting, and exhibit varying degrees of attributes from the *Melicope elleryana* or *Melicope hayesii* species including for example essential oils; and/or combinations thereof; and/or (4) mixtures of *Melicope elleryana* and *Melicope hayesii* materials. Brophy, *J. Essent. Oil Res.* (2004), vol. 16, pp 286-293, hereby incorporated by reference in its entirety, discloses the essential oil profile for *Melicope elleryana* and *Melicope hayesii*. In one embodiment, *Melicope* may include plants or extracts having an essential oil profile that includes carophylene, bicyclogermacrene; zierone, and/or evidone. In one embodiment, the essential oil profile may include about 4.0 to about 6.0% by weight of carophyllene, about 0.5 to about 1.5% by weight of bicyclogermacrene, about 25 to about 30% by weight of zierone, and/or about 10 to about 15% by weight of evodone; and in another embodiment the essential oil profile may include, about 5.0 to about 6.0% by weight of carophyllene, about 0.75 to about 1.25% by weight of bicyclogermacrene, about 26 to about 29.5% by weight of zierone, and/or about 11 to about 15% by weight of evodone. In a further embodiment, the essential oil profile of *Melicope* may include about 4.0 to about 6.0% by weight of carophyllene, about 0.5 to about 1.5% by weight of bicyclogermacrene, about 25 to about 30% by weight of zierone, and about 10 to about 15% by weight of evodone; and in another embodiment the essential oil profile may include, about 5.0 to about 6.0% by weight of carophyllene, about 0.75 to about 1.25% by weight of bicyclogermacrene, about 26 to about 29.5% by weight of zierone, and about 11 to about 15% by weight of evodone.

"Over-production of lipids" or "lipid over-production" refers to any production or secretion of oils and/or production or deposition of subcutaneous fat that is in excess of that desired by the individual. For example lipid over-production includes excess production, secretion, or accumulation of sebum, as well as excess production or accumulation of subcutaneous fat, such as cellulite.

"Prevention" as used herein, as well as related terms such as "prevent" or "preventing," refer to affording skin not yet affected by the condition a benefit that serves to avoid, delay, forestall, minimize, or reduce the recurrence/onset of one or more unwanted features associated with the skin condition to be prevented. Such preventative benefits include, for example, delaying development and/or recurrence of the condition, or reducing the duration, severity, or intensity of one or more unwanted features associated with the condition if it eventually develops. Use of the term "prevention" is not meant to imply that all subjects in a subject population administered the cosmetic composition will never be affected by or develop the cosmetic or dermatologic conditions, damage, effect, or symptom, but rather that the subject population will exhibit a reduction in the cosmetic or dermatologic damages, effects, or symptoms. For example, many flu vaccines are not 100% effective at preventing flu in those administered the vaccine. Preventing lipid over-production refers to affording not yet affected skin a benefit that serves to avoid, delay, forestall, or minimize one or more unwanted features associated with lipid over-production, such as reducing the extent of oiliness, severity of acne, or lumpiness of cellulite, that eventually develops at the treated area.

The term "reducing the appearance of excess lipids" is meant herein to refer to any detectable reduction in skin lipids, e.g., a reduction visible to the naked eye, that occurs after contacting the skin of an individual with a treatment regimen comprising a *Melicope* extract. As an example, this may refer to the oiliness/shine of hyperseborrhoeic skin or the "orange peel" or "cottage cheese" appearance of the skin The term "reducing lipid production" is used herein to mean a detectable lowering of the amount of lipids synthesized by a sebocyte/adipocyte exposed to a *Melicope* extract as compared to the amount of lipids synthesized in the absence of such an inhibiting compound. The term "reduction" as used herein in relation to lipids means the complete prevention, control of secretion, or a degree of reduction of the formation of lipids, respectively. The term "lowering" may refer to about a 10% to about a 100% decrease in the amount of lipids thereby synthesized. In one embodiment, the term "lowering" refers to about a 25% to about a 100% decrease in the amount of lipids synthesized. In another embodiment, the term "lowering" refers to about a 35% to about 100% decrease in the amount of lipids synthesized. In a further embodiment, the term "lowering" refers to about a 45% to about a 100% decrease in the amount of lipids synthesized. The terms lowering, reducing, decreasing, suppressing and inhibiting, when used in relation to lipid production, are intended to be used interchangeably. Such reduction in lipid production may be evaluated subjectively or by using assays including, but not limited to, in vitro, ex vivo, animal models, and/or clinical models known to those skilled in the art. For example, the reduction of lipid synthesis may be established using methods known to those skilled in the art including, but not limited to, human sebocyte/adipocyte cultures, Rat/mouse preputial models, hamster flank/ear models and or clinical models. See Examples 2, 3, and 5 below and K. R. Smith and D. M. Thiboutot, *Thematic review series: Skin Lipids Sebaceous gland lipids: friend or foe?*, Journal of Lipid Research Volume 49, 2008 271, hereby incorporated by reference in its entirety for all purposes. See also, U.S. Patent Application Publication No. 20050053631, hereby incorporated by reference in its entirety for all purposes.

The term "skin" as used herein includes the skin on or in the face, mouth, neck, chest, back, arms, hands, legs, and scalp.

"Treatment" as used herein, as well as related terms such as "treat" or "treating," refers to eradicating, reducing, ameliorating, or reversing one or more of the unwanted features associated with the skin condition being treated, such that the consumer perceives an improvement in the appearance of the skin or other treatment benefit with respect to the condition. Treating lipid over-production refers to eradicating, reducing, ameliorating, or reversing one or more of the unwanted features associated with over-production of lipids. Unwanted features associated with over-production of sebum, e.g., include oily, shiny, acne-prone skin, oily scalp, oily hair, dandruff-prone hair, enlarged pores, or undesirable body odors associated with the over-production of lipids. Unwanted features associated with over-production of subcutaneous fat, e.g., include unsightly areas of cellulite. Treatment benefits include, e.g., reducing the oily appearance of affected skin or hair, controlling surface oil, balancing sebum in oily-prone skin, visibly minimizing pores, reducing the incidence of acne (i.e., clogged pores, comedones, acne vulgaris, acne lesions, cystic acne, etc.), reducing undesirable body odor due to accumulation of excess sebum, reducing undesirable body fat, or improving the appearance of areas affected by cellulite deposition.

All percentages are by weight based on the total weight of the composition, unless otherwise indicated.

Cosmetic Compositions

The cosmetic compositions used in the method of the current invention comprise a botanical component derived from a *Melicope* plant. The *Melicope* plant may be in any form including, but not limited to, the whole plant, a dried plant, a ground plant or parts thereof, including but not limited to, seeds, needles, leaves, roots, bark, cones, stems, rhizomes, callus cells, protoplasts, organs and organ systems, and meristems, an extract, a dried extract, a synthetic extract, or components and/or constituents found in, or isolated from, the plant, and/or portions of the plant, or extracts derived either directly or synthetically from the plant, or any combinations thereof. In one embodiment, the cosmetic compositions used in this invention the botanical component is derived directly from the *Melicope* plants. The botanical component may be in a pure form, a semi-pure form, or unpurified form. The *Melicope* botanical component may be in the form of a liquid, a semi-solid, or a solid consistency. In one embodiment the botanical component may be an essential oil.

In one embodiment, the raw materials are collected from the leaves and terminal branchlets of the *Melicope* plants. In certain embodiments, the raw materials collected from the *Melicope* plants are ground to small particle sizes. In addition, the raw materials may be dried to reduce water content.

The raw materials may be air-dried, oven-dried, rotary evaporated under vacuum, lyophilized, or dried by any other suitable method known in the art.

The *Melicope* extract may be obtained by distilling the raw materials with a stripping agent. The stripping agent may be a liquid that is miscible, immiscible, or partially miscible with the desired extract from *Melicope*. Suitable stripping agents include, but are not limited to the following: water; alcohols (such as methanol, ethanol, propanol, butanol and the like); glycols; ethers (such as diethyl ether, dipropyl ether, and the like); esters (such as butyl acetate, ethyl acetate, and the like); ketones (such as acetone, ethyl methyl ketone, and the like); dimethyl sulfoxide; acetonitrile; other organic solvents; and combinations thereof. In one embodiment, the stripping agent is immiscible with the desired extract (e.g., essential oil) from *Melicope*. In one embodiment, the stripping agent is water. In a further embodiment, the *Melicope* extract is obtained by steam distillation. The *Melicope* extract (e.g., essential oil) may be collected by phase separation from the stripping agent. It is believed that the stripping agent increases the overall vapor pressure of a distillation system for obtaining an extract of *Melicope* and thereby reduces the boiling point of the desired product, the *Melicope* extract (or specifically, the *Melicope* essential oil).

In other embodiments, the *Melicope* botanical component may be in the form of an extract obtained by solvent extraction, in one embodiment obtained by an organic solvent extraction. Briefly, the organic solvent extraction method involves washing and extracting the raw materials, which may be whole or ground into small particle sizes, using an organic solvent. Non-limiting examples of organic solvents include methanol, ethanol, isopropanol, dichloromethane, chloroform, hexane, xylene, and petroleum ether. An extracting machine may be used for organic solvent extraction as is well known in the field. The raw materials are pushed slowly into the extracting machine by a thruster. Organic solvent (e.g., ethanol) may be added into the machine through a solvent inlet at the top of a waste discharge outlet. Due to the difference in gravity and equilibrium, the solvent flows toward the raw material inlet, soaks the materials and flows out from the opposite side of the solvent inlet. Since the plant materials and the solvent move in opposite directions against each other, the plant materials are constantly immersed in a solution that contains a low-concentration of extract. As a result of equilibrium, high yield of plant constituent(s) may be achieved by continuously extracting the plant material against the low-concentration solution.

An extraction time suitable to extract the *Melicope* plant constituents is used, typically between about 1-10 hours, in one embodiment between about 2-8 hours, and in another embodiment between about 3-6 hours. The temperature of extraction is between about 30° C.-100° C., in one embodiment between about 40° C.-70° C., and in another embodiment between about 50° C.-60° C. The collected extract is then fine-filtered to remove debris, and may be used directly, or is concentrated, for example by distilling the solvent or by other conventional processing. The solution of extract actives may be rotary evaporated under vacuum or lyophilized. A typical extract's actives content is above about 25%, in one embodiment it is above 50%, and the extract can also be provided as an essential oil or a concentrate having a semi-solid or solid consistency.

Similarly, aqueous-organic solvent extraction involves initially collecting raw materials from the *Melicope* plants, which may be whole or ground into small particle sizes. The ground plant material is soaked in aqueous solution that is acidic or alkaline, depending on the solubility and stability of the desired extract under acidic or alkaline (basic) conditions. For extraction under acidic conditions, an acid such as hydrochloric acid or sulfuric acid is added to water, e.g., at a concentration of about 3% (w/v). For extraction under alkaline conditions, an alkali such as sodium hydroxide or sodium carbonate is added to water. The extraction time and temperature of extraction are typically similar to that used in the organic solvent extraction method described above.

The extract is then collected and fine-filtered to remove debris. Alkaline agents (e.g., ammonia) or acidifying agents (e.g., sulfuric acid) may be added to the extract to neutralize the solution by adjusting the pH, depending on the acidity or alkalinity of the collected extract. The aqueous extract may be used directly, in concentrated or dried form. Alternatively, organic solvent may then be added to the neutralized solution to transfer the extract from an aqueous phase to an organic phase. Examples of such organic solvents include, but are not limited to, ethanol, isopropanol, butanol, pentanol, hexanol, and xylene. The extract comprising the transferred extract actives dissolved in organic solvent may be used directly as an essential oil or a concentrate, or dried by a number of different means, such as, for example, air-drying, oven-drying, rotary evaporating under vacuum or lyophilizing to a semi-solid or solid consistency.

It should also be noted that different plants containing different constituents can be mixed and extracted together with *Melicope*. This process of mixed extraction can be used for extracting those plants containing constituents with similar solubility as *Melicope* in the solvent used for extraction, such as ethanol. The mixture of extracts can be concentrated and stored in an appropriate solvent.

In another embodiment, the *Melicope* extract as used herein, also includes "synthetic" extracts, i.e., various combinations of known *Melicope* plant components and/or constituents that are combined to substantially mimic the composition and/or activity of a *Melicope* plant extract of natural origin. The synthetic extracts may have substantially the same number of active components as a natural *Melicope* plant material. The correspondence of the numerical incidence of actives between the synthetic extracts and the natural *Melicope* plant material may also be described in terms of "percent commonality." The synthetic extract has about 50 percent or more commonality to the chemical composition of a plant or natural extract. In other words, the synthetic extract has about 50 percent or more of the active ingredients found in the plant or a natural extract. More preferably, the chemical composition of the synthetic extract has about 70 percent or more commonality to the chemical composition of a plant or a natural extract. Optimally, a synthetic extract has about 90 percent or more commonality to the chemical composition of a plant or a natural extract.

The compositions according to the invention can be formulated in a variety of forms for topical application and will comprise from about 0.0001% to about 90% by weight of an extract of *Melicope*, or will comprise from about 0.0005% to about 25% by weight, or, still further, from about 0.001% to about 10% by weight. The composition may comprise a *Melicope* extract within a range from about 0.005%, 0.01%, 0.05%, 0.1%, 0.25%, 0.5%, 0.75% or 1% up to 5%, 7.5% or 10% by weight of the total composition. The compositions will comprise an effective amount of an extract of *Melicope*, by which is meant an amount sufficient to reduce and/or inhibit the appearance of excess lipids and/or the over-production of lipids in a given area of skin when topically applied thereto. The above amounts refer to an "active amount" of a *Melicope* extract.

In accordance with the invention, compositions comprising components from the *Melicope* plant include, but are not limited to, topically applied formulations, anti-oxidants, anti-inflammatories, sunscreens, cosmetics (including makeup), formulations for reducing excess subcutaneous fats (e.g., anti-cellulite creams), or excess sebum reduction formulations for treating oily skin or hair, enlarged pores, or acne-prone skin, personal care products (e.g., antiperspirants or deodorants for controlling body odor), topicals, skin penetration enhancers, and the like. Also in accordance with this invention, the *Melicope* plant components and additional ingredients comprising such compositions may be formulated in a variety of product forms. The compositions may be prepared in targeted delivery systems, e.g. creams, lotions, gels, toners, serums, transdermal patches, and the like, particularly for topical administration. Targeted delivery and/or penetration enhancement may also be achieved by iontophoresis.

The present invention further provides that compositions comprising the *Melicope* plant components may be topically administered for targeted delivery for the current method. The method of the current invention is suitable for all skin types, such as sensitive, normal, oily, or combination. In particular embodiments, the compositions may be for oily skin or hair types. The compositions are applied to the skin or hair for a period of time sufficient to improve the aesthetic appearance of conditions related to skin, including unwanted features associated with lipid over-production, e.g., oily skin or hair, enlarged pores, acne-prone skin, body odors due to over-production of lipids, and/or cellulite. The compositions may be applied topically once, twice, or more daily, and in one embodiment once a day. The daily application may be applied for a period of one week, two weeks, four weeks, or more.

The compositions may be formulated into liposomes which can comprise other additives or substances, and/or which can be modified to more specifically reach or remain at a site following administration. The compositions of the present invention yield improvements to the aesthetic appearance by treating at least one of the unwanted features related to lipid over-production.

Another embodiment of the method of the current invention encompasses compositions comprising a cosmetically or dermatologically acceptable formulation which is suitable for contact with living animal tissue, including human tissue, with virtually no adverse physiological effect to the user. Compositions embraced by this invention can be provided in any cosmetically and/or dermatologically suitable form, such as a lotion or cream, but also in an anhydrous or aqueous base, as well as in a sprayable liquid form. Other suitable cosmetic product forms for the compositions used in this invention include, for example, an emulsion, a cream, a balm, a gloss, a lotion, a mask, a serum, a toner, an ointment, a mousse, a patch, a pomade, a solution, a spray, a wax-based stick, or a towelette. In addition, the compositions can include one or more compatible cosmetically acceptable adjuvants commonly used and known by the skilled practitioner, such as colorants, fragrances, emollients, humectants, preservatives, vitamins, chelators, thickeners, *perilla* oil or *perilla* seed oil (WO 01/66067 to a "Method of Treating a Skin Condition," incorporated herewith in its entirety for all purposes) and the like, as well as other botanicals such as aloe, chamomile, and the like, and as further described below.

Also, embraced by the invention are transdermal modes of delivery, such as patches and the like, with or without a suitable penetration enhancer. The methods and compositions embodied by the invention provide a means by which the *Melicope* components can be effectively administered in a transdermal system. Accordingly, a transdermal means of delivering a composition or formulation (often with a penetration enhancing composition) to the skin is that of the transdermal patch or a similar device as known and described in the art. Transdermal patches are designed to deliver an effective amount of compound across a user's skin. Transdermal patches typically involve a liquid, gel, solid matrix, or pressure-sensitive adhesive carrier into which the *Melicope* extract may be incorporated. Patch formulations and preparations are well known in the art. See for example "Dermatological and Transdermal Formulations" (Drugs and the Pharmaceutical Sciences, Vol 119) by Kenneth A Walters (Editor), Marcel Dekker and "Transdermal Drug Delivery" (Drugs & the Pharmaceutical Sciences) by Richard H. Guy (Editor), Jonathan Hadgraft (Editor) 2nd Rev & ex edition Marcel Dekker and "Mechanisms of Transdermal Drug Delivery" (Drugs & the Pharmaceutical Sciences, Vol 83) edited by Russell O. Potts and Richard H. Guy (1997). Examples of such devices are disclosed in U.S. Pat. Nos. 5,146,846; 5,223,262; 4,820,724; 4,379,454; and 4,956,171; and U.S. Patent Publication No. US20110300198, all of which are incorporated herein by reference and such descriptions are not meant to be limiting. The transdermal mode of storing and delivering the compositions onto the skin, including hair, and forming the active composition is convenient and well-suited for the purposes of an embodiment of the present invention. In one embodiment, the application occurs through a sustained release vehicle, carrier, or diluent, e.g., a topically applied sustained released patch. When a topical patch is used, the patch may be applied to the desired area for extended period of time. In one embodiment, the extended period of time may be greater than one hour, in a further embodiment the extended period of time is overnight, i.e., when the user is sleeping. Additionally, the transdermal patches may be formulated to provide extended benefits for a period of about 1-7 days, in one embodiment about 2 to 7 days, and in another embodiment about 3-7 days. Such extended wear patches may be particularly well suited to treat, ameliorate, and/or prevent cellulite and/or excess body fat and may be used to provide continuous treatment to "problem" areas such as cellulite and excess fat found on the torso, thighs, and buttocks referred to as "love handles," "muffin tops," etc.

The topical compositions can include one or more cosmetically acceptable vehicles. Such vehicles may take the form of any known in the art suitable for application to skin and may include water (e.g., deionized water); vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, dimethicone, dimethicone cross-polymer, polysiloxanes and their derivatives, such as organomodified derivatives; hydrocarbon oils such as mineral oil, petrolatum, isoeicosane and polyisobutene; polyols such as propylene glycol, glycerin, butylene glycol, pentylene glycol and hexylene glycol; waxes such as beeswax and botanical waxes; or any combinations or mixtures of the foregoing.

The vehicle may comprise an aqueous phase, an oil phase, an alcohol, a silicone phase or mixtures thereof. The cosmetically acceptable vehicle may also comprise an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. The emulsion may include an emulsifier, such as a nonionic, anionic or amphoteric surfactant.

In one embodiment, the oil phase of the emulsion may have one or more organic compounds, including emollients; humectants (such as butylene glycol, propylene glycol, Methyl gluceth-20, and glycerin); other water-dispersible or water-soluble components including thickeners such as vee-gum or hydroxyalkyl cellulose; gelling agents, such as high MW polyacrylic acid, i.e. CARBOPOL 934; and mixtures thereof. The emulsion may have one or more emulsifiers capable of emulsifying the various components present in the composition.

The compounds suitable for use in the oil phase include without limitation, vegetable oils; esters such as octyl palmitate, isopropyl myristate and isopropyl palmitate; ethers such as dicapryl ether; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; natural or synthetic waxes; and the like. Suitable hydrophobic hydrocarbon oils may be saturated or unsaturated, have an aliphatic character and be straight or branched chained or contain alicyclic or aromatic rings. The oil-containing phase may be composed of a singular oil or mixtures of different oils.

Hydrocarbon oils include those having 6-20 carbon atoms, and in one embodiment those having 10-16 carbon atoms. Representative hydrocarbons include decane, dodecane, tetradecane, tridecane, and $C_{8-20}$ isoparaffins. Paraffinic hydrocarbons are available from Exxon under the ISOPARS trademark, and from the Permethyl Corporation. In addition, $C_{8-20}$ paraffinic hydrocarbons such as $C_{12}$ isoparaffin (isododecane) manufactured by the Permethyl Corporation having the tradename Permethyl 99A™ are also contemplated to be suitable. Various commercially available $C_{16}$ isoparaffins, such as isohexadecane (having the tradename Permethyl®) are also suitable. Examples of volatile hydrocarbons include polydecanes such as isododecane and isodecane, including for example, Permethyl-99A (Presperse Inc.) and the $C_7$-$C_8$ through $C_{12}$-$C_{15}$ isoparaffins such as the Isopar Series available from Exxon Chemicals. A representative hydrocarbon solvent is isodecane.

The oil phase may comprise one or more waxes, including for example, rice bran wax, carnauba wax, ouricurry wax, candelilla wax, montan waxes, sugar cane waxes, ozokerite, polyethylene waxes, Fischer-Tropsch waxes, beeswax, microcrystalline wax, silicone waxes, fluorinated waxes, and any combination thereof.

Non-limiting emulsifiers include emulsifying waxes, emulsifying polyhydric alcohols, polyether polyols, polyethers, mono- or di-ester of polyols, ethylene glycol monostearates, glycerin mono-stearates, glycerin di-stearates, silicone-containing emulsifiers, soya sterols, fatty alcohols such as cetyl alcohol, acrylates, fatty acids such as stearic acid, fatty acid salts, and mixtures thereof. Emulsifiers may include soya sterol, cetyl alcohol, stearic acid, emulsifying wax, acrylates, silicone containing emulsifiers and mixtures thereof. Other specific emulsifiers that can be used in the composition of the present invention include, but are not limited to, one or more of the following: $C_{10-30}$ alkyl acrylate crosspolymer; Dimethicone PEG-7 isostearate, acrylamide copolymer; mineral oil; sorbitan esters; polyglyceryl-3-diisostearate; sorbitan monostearate, sorbitan tristearate, sorbitan sesquioleate, sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, Steareth-10, and Steareth-20, to name a few. Additional emulsifiers are provided in the INCI Ingredient Dictionary and Handbook $11^{th}$ Edition 2006, the disclosure of which is hereby incorporated by reference.

These emulsifiers typically will be present in the composition in an amount from about 0.001% to about 10% by weight, or an amount from about 0.01% to about 5% by weight, or, still further, from about 0.1% to about 3% by weight.

The oil phase may comprise one or more volatile and/or non-volatile silicone oils. Volatile silicones include cyclic and linear volatile dimethylsiloxane silicones. In one embodiment, the volatile silicones may include cyclodimethicones, including tetramer ($D_4$), pentamer ($D_5$), and hexamer ($D_6$) cyclomethicones, or mixtures thereof. Particular mention may be made of the volatile cyclomethicone-hexamethyl cyclotrisiloxane, octamethyl-cyclotetrasiloxane, and decamethyl-cyclopentasiloxane. Suitable dimethicones are available from Dow Corning under the name Dow Corning 200® Fluid and have viscosities ranging from 0.65 to 600,000 centistokes or higher. Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as hexamethyldisiloxane, octamethyltrisiloxane, decamethyltetrasiloxane, and dodecamethylpentasiloxane, to name a few.

Non-volatile silicone oils will typically comprise polyalkylsiloxanes, polyarylsiloxanes, polyalkylarylsiloxanes, or mixtures thereof. Polydimethylsiloxanes are non-volatile silicone oils. The non-volatile silicone oils will typically have a viscosity from about 10 to about 60,000 centistokes at 25° C., in one embodiment between about 10 and about 10,000 centistokes, and in another embodiment between about 10 and about 500 centistokes; and a boiling point greater than 250° C. at atmospheric pressure. Non limiting examples include dimethyl polysiloxane (dimethicone), phenyl trimethicone, and diphenyldimethicone. The volatile and non-volatile silicone oils may optionally be substituted with various functional groups such as alkyl, aryl, amine groups, vinyl, hydroxyl, haloalkyl groups, alkylaryl groups, and acrylate groups, to name a few.

The water-in-silicone emulsion may be emulsified with a nonionic surfactant (emulsifier) such as, for example, polydiorganosiloxane-polyoxyalkylene block copolymers, including those described in U.S. Pat. No. 4,122,029, the disclosure of which is hereby incorporated by reference. These emulsifiers generally comprise a polydiorganosiloxane backbone, typically polydimethylsiloxane, having side chains comprising -(EO)m- and/or —(PO)n- groups, where EO is ethyleneoxy and PO is 1,2-propyleneoxy, the side chains being typically capped or terminated with hydrogen or lower alkyl groups (e.g., C1-6, typically C1-3). Other suitable water-in-silicone emulsifiers are disclosed in U.S. Pat. No. 6,685,952, the disclosure of which is hereby incorporated by reference herein. Commercially available water-in-silicone emulsifiers include those available from Dow Corning under the trade designations 3225C and 5225C FORMULATION AID; SILICONE SF-1528 available from General Electric; ABIL EM 90 and EM 97, available from Goldschmidt Chemical Corporation (Hopewell, Va.); and the SILWET series of emulsifiers sold by OSI Specialties (Danbury, Conn.).

Examples of water-in-silicone emulsifiers include, but are not limited to, dimethicone PEG 10/15 crosspolymer, dimethicone copolyol, cetyl dimethicone copolyol, PEG-15 lauryl dimethicone crosspolymer, laurylmethicone crosspolymer, cyclomethicone and dimethicone copolyol, dimethicone copolyol (and) caprylic/capric triglycerides, polyglyceryl-4 isostearate (and) cetyl dimethicone copolyol (and) hexyl laurate, and dimethicone copolyol (and) cyclopentasiloxane. Examples of water-in-silicone emulsifiers may include, without limitation, PEG/PPG-18/18 dimethicone (trade name 5225C, Dow Corning), PEG/PPG-19/19 dimethicone (trade name BY25-337, Dow Corning), Cetyl PEG/PPG-10/1 dimethicone (trade name Abil EM-90, Goldschmidt Chemical Corporation), PEG-12 dimethicone (trade name SF 1288, General Electric), lauryl PEG/PPG-18/18 methicone (trade name 5200 FORMULATION AID, Dow Corning), PEG-12 dimethicone crosspolymer (trade name 9010 and 9011 silicone elastomer blend, Dow Corning), PEG-10 dimethicone crosspolymer (trade name KSG-20, Shin-Etsu), dimethicone PEG-10/15 crosspolymer (trade name KSG-210, Shin-Etsu), and dimethicone PEG-7 isostearate.

The water-in-silicone emulsifiers typically will be present in the composition in an amount from about 0.001% to about 10% by weight, in particular in an amount from about 0.01% to about 5% by weight, and in one embodiment, below 1% by weight.

The aqueous phase of the emulsion may include one or more additional solvents, including lower alcohols, such as ethanol, isopropanol, and the like. The volatile solvent may also be a cosmetically acceptable ester such as butyl acetate or ethyl acetate; ketones such as acetone or ethyl methyl ketone; or the like.

The oil-containing phase will typically comprise from about 10% to about 99%, in one embodiment from about 20% to about 85%, and in another embodiment from about 30% to about 70% by weight, based on the total weight of the emulsion, and the aqueous phase will typically comprise from about 1% to about 90%, in one embodiment from about 5% to about 70%, and in another embodiment from about 20% to about 60% by weight of the total emulsion. The aqueous phase will typically comprise from about 25% to about 100%, more typically from about 50% to about 95% by weight water.

The compositions may include liposomes. The liposomes may comprise other additives or substances and/or may be modified to more specifically reach or remain at a site following administration.

The daily doses recommended in conformity with the invention range from 0.5 to 2600 mg/day, and in one embodiment from 5 to 1200 mg/day of *Melicope* extract. The compositions of the invention can be taken for several days, weeks or months. The regimen of treatment can be repeated many times in a year and can even be continuous.

The composition may optionally comprise other cosmetic actives and excipients, obvious to those skilled in the art including, but not limited to, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfolients, lubricants, fragrances, colorants, depigmenting agents, hypopigmenting agents, preservatives (e.g., DMDM Hydantoin/Iodopropynylbutylcarbonate), stabilizers, pharmaceutical agents, photostabilizing agents, neutralizers (e.g., triethanolamine) and mixtures thereof. In addition to the foregoing, the cosmetic compositions of the invention may contain any other compound for the treatment of skin disorders.

In some embodiments, the cosmetic compositions for treatment and/or prevention of lipid over-production, e.g., reduction of sebum output or cellulite, can further comprise at least one other anti-lipid agent. For example, the cosmetic composition comprising a *Melicope* extract in an amount effective to treat and/or prevent lipid over-production may further comprise at least one other anti-lipid agent. Examples include, without limitation, certain anti-acne agents and other PPAR inhibitors, e.g., extracts from *Alisma orientate*, see, e.g., U.S. Pat. No. 7,410,658; a modified yeast peptide fraction comprising a metal-complexed peptide, see e.g., U.S. Patent publication No. US20110052517, as well as known lipases or lipolitics, and combinations thereof. Further, it is contemplated that synergistic improvements may be obtained with combinations of one or more such additional anti-lipid agents with compositions of the instant invention, in some embodiments.

In some embodiments, the cosmetic compositions for combating signs of unwanted subcutaneous fat can further comprise additional anti-lipid agents. For example, the cosmetic composition comprising a Carnitine Palmitoyl Transferase-1 (CPT-1) stimulator (e.g. the leaf extract of *Averrhoa carambola*) in an amount effective (or amounts effective) to improve the appearance of skin may further comprise at least one other anti-lipid agent, including one other anti-cellulite agent. It is contemplated that synergistic improvements may be obtained with such combinations, in some embodiments.

Exemplary anti-cellulite agents include, without limitation, phosphodiesterase inhibitors such as xanthine analogs, caffeine, aminophylline, and theophylline; adenylate cyclase activators, such as forskolin and *Coleus forskohlii* extract; lipolysis stimulators, such as hawthorne extract and cola extract; beta adrenergic receptor agonists such as isoproterenol; alpha-2-adrenergic antagonists such as yohimbine and *Ginkgo biloba* extract; *perilla* oil (see, e.g., U.S. Pat. No. 7,410,658); carnitine and/or creatine (see, e.g., US 2007/0264205 entitled "Cosmetic Composition having Carnitine Creatinate and Methods for Using," incorporated herein by reference in its entirety), and combinations thereof. In some embodiments, additional actives may include a collagen stimulator and/or an elastin stimulator, e.g., a substance that stimulates elastin production, and/or a glycosaminoglycan enhancer. Examples of collagen, elastin, and glycosaminoglycan enhancers include, e.g., fennel extract, carrot extract, and alfalfa extract, and combinations thereof. In some embodiments the additional actives may include a collagenase inhibitor and/or elastase inhibitor. In some embodiments the invention relates to synergistic action of one or more compositions described herein with *perilla* oil, e.g., to provide enhanced anti-cellulite benefits to skin.

In some embodiments the cosmetic compositions can further comprise at least one collagen and/or elastin stimulator. Such collagen or elastin stimulators are effective in, for example, providing improvement in procollagen and/or collagen production and/or improvement in maintenance and remodeling of elastin.

Colorants may include, for example, organic and inorganic pigments and pearlescent agents. Suitable inorganic pigments include, but are not limited to, titanium oxide, zirconium oxide, and cerium oxide, as well as zinc oxide, iron oxide, chromium oxide and ferric blue. Suitable organic pigments include barium, strontium, calcium, aluminium lakes and carbon black. Suitable pearlescent agents include mica coated with titanium oxide, iron oxide, or natural pigments.

Various fillers and additional components may be added. Fillers are normally present in an amount of about 0 weight % to about 20 weight %, based on the total weight of the composition, and in one embodiment about 0.1 weight % to about 10 weight %. Suitable fillers include without limitation the following: silica, treated silica, talc, zinc stearate, mica, kaolin, Nylon powders such as Orgasol™, polyethylene powder, Teflon™, starch, boron nitride, copolymer microspheres such as Expancel™ (Nobel Industries), Polytrap™ (Dow Corning) and silicone resin microbeads (Tospearl™ from Toshiba), and the like.

In one embodiment of the invention, the compositions may include additional skin actives such as, but not limited to, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, salicylic acid or salicylates, thiodipropionic acid or esters thereof, and advanced glycation end-product (AGE) inhibitors.

In a specific embodiment, the composition may comprise at least one additional botanical, such as, for example, a botanical extract, an essential oil, or the plant itself. Suitable botanicals include, without limitation, extracts from *Abies pindrow, Acacia catechu, Anogeissus latifolia, Asmunda japonica, Azadirachta indica, Butea frondosa, Butea monosperma, Cedrus deodara, Emblica officinalis, Ficus benghalensis, Glycyrrhiza glabra, Ilex purpurea Hassk, Inula racemosa, Ligusticum chuangxiong, Ligusticum lucidum, Mallotus philippinensis, Mimusops elengi, Morinda citrifolia, Moringa oleifera, Naringi crenulata, Nerium indicum, Psoralea corylifolia, Stenoloma chusana, Terminalia bellerica,* tomato glycolipid and mixtures thereof.

The composition may comprise additional active ingredients having anti-aging benefits, as it is contemplated that synergistic improvements may be obtained with such combinations. Exemplary anti-aging components include, without limitation, botanicals (e.g., *Butea Frondosa* extract); thiodipropionic acid (TDPA) and esters thereof; retinoids (e.g., all-trans retinoic acid, 9-cis retinoic acid, phytanic acid and others); hydroxy acids (including alpha-hydroxyacids and beta-hydroxyacids), salicylic acid and salicylates; exfoliating agents (e.g., glycolic acid, 3,6,9-trioxaundecanedioic acid, etc.); estrogen synthetase stimulating compounds (e.g., caffeine and derivatives); compounds capable of inhibiting 5 alpha-reductase activity (e.g., linolenic acid, linoleic acid, finasteride, and mixtures thereof); barrier function enhancing agents (e.g., ceramides, glycerides, cholesterol and its esters, alpha-hydroxy and omega-hydroxy fatty acids and esters thereof, etc.); collagenase inhibitors; and elastase inhibitors; to name a few.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

In another embodiment, the topical compositions of the present invention may also include one or more of the following: a skin penetration enhancer, an emollient, a skin plumper, an optical diffuser, a sunscreen, an exfoliating agent, and an antioxidant.

An emollient provides the functional benefits of enhancing skin texture (smoothness) and reducing the appearance of fine lines and coarse wrinkles. Examples include isopropyl myristate, petrolatum, isopropyl lanolate, silicones (e.g., methicone, dimethicone), oils, mineral oils, fatty acid esters, cetyl ethylhexanoate, $C_{12-15}$ alkyl benzoate, isopropyl isostearate, diisopropyl dimer dillinoeate, or any mixtures thereof. The emollient may be present from about 0.1 wt % to about 50 wt % of the total weight of the composition.

A skin plumper serves as a collagen enhancer to the skin. An example of a suitable skin plumper is palmitoyl oligopeptide. Other skin plumpers are collagen and/or other glycosaminoglycan (GAG) enhancing agents. When present, the skin plumper may comprise from about 0.1 wt % to about 20 wt % of the total weight of the composition.

An optical diffuser is a particle that changes the surface optometrics of skin, resulting in a visual blurring and softening of, for example, lines and wrinkles. Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. When present, the optical diffuser may be present from about 0.01 wt % to about 20 wt % of the total weight of the composition.

A sunscreen for protecting the skin from damaging ultraviolet rays may also be included. Sunscreens may include those with a broad range of UVB and UVA protection, such as octocrylene, avobenzone (Parsol 1789), octyl methoxycinnamate, octyl salicylate, oxybenzone, homosylate, benzophenone, camphor derivatives, zinc oxide, and titanium dioxide. When present, the sunscreen may comprise from about 0.01 wt % to about 70 wt % of the composition.

Suitable exfoliating agents include, for example, alpha-hydroxyacids, beta-hydroxyacids, oxaacids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. In one embodiment the exfoliating agent may be glycolic acid. When present, the exfoliating agent may comprise from about 0.1 wt % to about 80 wt % of the composition.

An antioxidant functions, among other things, to scavenge free radicals from skin to protect the skin from environmental aggressors. Examples of antioxidants that may be used in the present compositions include compounds having phenolic hydroxy functions, such as ascorbic acid and its derivatives/esters; alpha-hydroxyacids; beta-carotene; catechins; curcumin; ferulic acid derivatives (e.g. ethyl ferulate, sodium ferulate); gallic acid derivatives (e.g., propyl gallate); lycopene; reductic acid; rosmarinic acid; tannic acid; tetrahydrocurcumin; tocopherol and its derivatives (e.g., tocopheryl acetate); uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may comprise an antioxidant from about 0.001 wt % to about 10 wt %, and in one embodiment from about 0.01 wt % to about 5 wt %, of the total weight of the composition.

Other conventional additives include: vitamins, such as tocopherol and ascorbic acid; vitamin derivatives such as ascorbyl monopalmitate; thickeners such as hydroxyalkyl cellulose; gelling agents; structuring agents such as bentonite, smectite, magnesium aluminum silicate and lithium magnesium silicate; metal chelating agents such as EDTA; pigments such as zinc oxide and titanium dioxide; colorants; emollients; and humectants.

Further, for oral compositions suitable for administration in accordance with the current method may include additional active ingredients such as appetite suppressants, fat burners, and the like provided they are suitable for human consumption in order to provide prolonged or synergistic benefits.

In one embodiment, the composition may be essentially free of components having a strong oxidizing potential, including for example, organic or inorganic peroxides. "Essentially free of" these components means that the amounts present are insufficient to have a measurable impact on the lipid inhibiting activity of an extract of *Melicope*. In some embodiments, this will be, in relation to the amount of *Melicope*, less than 1% by weight.

In one embodiment, the composition of the invention comprising an extract of *Melicope* may have a pH between about 1 and about 8. In certain embodiments, the pH of the composition will be acidic, i.e., less than 7.0, in one embodiment may be between about 2 and about 7, and in another embodiment may be between about 3.5 and about 5.5.

Method of Treating Lipid Over-Production

The invention provides a method for treating skin affected by lipid over-production by topically applying a composition comprising an extract of *Melicope*, in a cosmetically acceptable vehicle in one embodiment, over the affected area for a period of time sufficient to reduce, ameliorate, reverse or prevent dermatological signs of lipid over-production. This method is particularly useful for treating unwanted features associated with the over-production of lipids. In some embodiments, a composition comprising an effective amount of *Melicope* extract is topically applied to the skin, for example to an area of skin affected by lipid over-production. Areas affected by sebum over-production include oily areas of the skin, e.g., oily facial skin (especially in T-zone-forehead, nose, and chin) or an area of the scalp, as well as non-facial areas, such as the chest, neck, shoulders, and/or back. Areas affected by lipid over-production include areas of cellulite, such as areas of the skin having the "orange peel", "cottage cheese" or "mattress" appearance. In such uses the *Melicope* extract may be referred to as an "anti-lipid agent."

It is believed that the *Melicope* extract of the present invention may provide such benefits through one or more activities including, but not limited to, decreasing triglyceride levels in adipocytes/sebocytes, such as by bringing about one of more of a decrease in pre-adipocyte proliferation and/or adipocyte differentiation; a decrease in intracellular lipid and/or triglyceride production, storage, and/or accumulation, an increase in fatty acid oxidation, degradation and/or lipolysis; and/or reduced expression of lipogenic genes, in vitro or in vivo. Without wishing to be bound by a theory, it is believed that the *Melicope* extract can act to decrease PPAR-γ signaling and/or the up regulation of adipogenic genes responsive to PPAR-γ signaling, such as FAS and SCD-1, in sebocytes and/or adipocytes, thereby reducing lipid production and acting as anti-oil/sebum and/or anti-cellulite agent. For example, the current methods of using *Melicope* may act to decrease induction of PPAR-γ, so that less is available for signaling adipocyte differentiation and fat storage. In certain embodiments, the *Melicope* extract is administered in an amount sufficient to decrease PPAR-γ signaling in a given area of skin when topically applied thereto. In a further example, the current method of using *Melicope* may act to decrease signaling of FAS and/or SCD-1, so that less is available for signaling fatty acid and/or triglyceride synthesis. In certain embodiments, the *Melicope* extract is administered in an amount sufficient to decrease FAS and/or SCD-1 signaling in a given area of skin when topically applied thereto.

Generally, the improvement in the condition and/or aesthetic appearance is selected from the group consisting of: reducing lipid production by sebaceous glands; reducing lipid synthesis in subcutaneous adipose tissue; reducing triglyceride synthesis; reducing fatty acid synthesis; preventing and/or improving conditions related to skin associated with inhibited lipolysis; preventing and/or improving conditions related to skin associated with nonselective or partially selective PPAR receptor stimulators/up regulators; preventing and/or improving conditions related to skin associated with nonselective or partially selective up regulation of adipogeneic genes typically up regulated by PPAR-γ activation; preventing and/or improving conditions related to skin associated with nonselective or partially selective FAS stimulators/up regulators; preventing and/or improving conditions related to skin associated with nonselective or partially selective SCD-1 stimulators/up regulators; preventing, ameliorating or treating oily skin; preventing, ameliorating or treating oily hair; preventing, ameliorating or treating oily scalp; preventing, ameliorating or treating enlarged pores; preventing, ameliorating, or treating acne-prone skin; preventing, ameliorating or treating body odors associated with excess sebum production; preventing, ameliorating or treating cellulite in adults; reducing in the appearance of cellulite lumpiness and/or unevenness; reducing the pitting appearance of cellulite upon squeezing; reducing the extent of area affected by cellulite; preventing or delaying in recurrence of cellulite, preventing, ameliorating or treating excess accumulation or production of subcutaneous fat in adults; and improving skin texture associated with cellulite, and any combinations thereof.

Anti-Oil/Sebum Benefits

The method of the present invention provides an anti-oil/sebum effect so as to produce a visible or palpable improvement in skin affected by excess sebum. Such improvements include without limitation, the following:

(a) restoration of a matte finish to the skin;
(b) an evening of skin type;
(c) reduction in oily/greasy feel to skin and/or hair;
(d) reduction in the incidence of dandruff;
(e) reduction in the incidence of blocked/clogged pores;
(f) reduction in the incidence of comedones;
(g) reduction in the incidence of acne lesions;
(h) reduction in the area over-producing lipids;
(i) reduction in thickness of skin affected by over-production of lipids.

In use in accordance with the current method, an effective amount of a *Melicope* extract may be applied to exposed areas of the skin, from a suitable container or applicator and, if necessary, it is then spread over and/or rubbed into the skin using the hand or fingers or a suitable device. In accordance with the current cosmetic method, the composition may be applied as frequently as need to achieve the desired effects upon the skin. Thus, one will appreciate that the composition may be applied daily, in one embodiment multiple times daily, i.e. 2 or more times, and in another embodiment at least three times daily when an individual is experiencing the appearance of excess lipids. In such instances it may be desirable to combine the extracts of the current composition with known lipases and lipolytics to provide more immediate relief from the unwanted feature. Once the appearance of excess lipids has subsided, the individual may, in accordance with the current invention, scale back the frequency of the administration of the cosmetic composition to once daily, several times (2 to 6 times) a week or given the prolonged effect of *Melicope* extracts, as noted in exhibit 4B below, to once a week in order to maintain the desired complexion.

The composition may be applied in accordance with the current invention proactively and/or preventively to areas of the skin known to experience oiliness/greasiness. Such areas may include any area on the individual's skin he/she feels exhibits or in his/her personal experience exhibits over-production of lipids. Commonly such areas include the back, shoulders, chest, neck, hair, scalp, and face. In certain embodiments, the compositions incorporating *Melicope* extracts may be applied to the face and in other embodiments to the zone of the forehead, nose, and/or chin.

Further, the method of the current invention may be used to prevent and/or reduce the incidence of various conditions such as acne and/or dandruff associated with hyperseborrehic skin. A reduction in the incidence of these conditions includes, but is not limited to, a reduction in the frequency, a reduction in the severity, and/or reduction of the area over which such conditions occur. However, in one embodiment of the current method the compositions are not applied to an area of the skin currently experiencing the condition, i.e., exhibiting acne comedones, lesions, and/or cysts as well as flaking due to dandruff.

As noted above, several pharmaceuticals such as muscle stimulants and/or PPAR agonists may result in the side-effect of lipid over-production. Further, certain disease states that affect the autonomic nervous system such as stroke, Parkinson's disease, etc. may also cause lipid over-production. The method of the current invention may be used to ameliorate these occurrences and may be administered prior to and/or concomitantly with the pharmaceutical and/or disease state.

Anti-Cellulite Benefits

In some embodiments, a method is provided for improving the appearance of skin affected by subcutaneous lipid overproduction and/or accumulation, such as in the case of cellulite, where the method comprises topical application to affected skin of a *Melicope* extract in a cosmetically acceptable vehicle. Such improvements include without limitation, the following:

(a) reduction in appearance of cellulite lumpiness and/or unevenness;
(b) reduction in pitting appearance of cellulite upon squeezing;
(c) reduction in extent of area affected by cellulite;
(d) prevention or delay in recurrence of cellulite; and
(e) reduction in subcutaneous fat deposition and/or accumulation;

The compositions of the invention can be applied to skin in need of treatment, such as skin which suffers from a deficiency or loss in any of the foregoing attributes or which would otherwise benefit from the composition's anti-lipid effects, e.g., as described herein. For example, the *Melicope* extract, can be provided in a cosmetically acceptable vehicle, topically applied to a desired area of skin, and allowed to remain on the area in an amount effective to treat and/or prevent an unwanted feature or condition of the skin, and/or to improve the aesthetic appearance of the skin.

Cosmetic compositions taught herein can be applied to an area of skin affected by cellulite to improve the appearance of the skin. An improvement may involve a reduction in appearance of lumpiness and/or unevenness, characteristic of cellulite, in one embodiment reducing what is known as the "cottage cheese" or "orange peel" look. Further, areas of cellulite tend to bulge, pit, and dimple when squeezed or compressed, as occurs when legs are crossed when seated, which can worsen the appearance of cellulite areas. In some embodiments, an improvement involves a reduction in this pitting appearance of cellulite upon squeezing, so that the look of cellulite on the legs appears reduced even when sitting with the legs crossed. An improvement may also involve reducing the visible depth and/or intensity of cellulite. In certain embodiments, known evaluative scales can be used to determine the initial severity of the cellulite and gauge the improvement after treatment with the cosmetic compound of the current invention. One such scale is the Nurnberger-Muller scale, which provides a scale of: Stage 0—no dimpling when the subject is standing and lying down—a pinch test can show folds in the skin, but no cellulite is visible; Stage 1—no dimpling when the subject is standing or lying down however when pinched, the skin shows signs of cellulite; Stage 2—dimpling is present when standing only; and Stage 3—dimpling is visible when both standing and lying down; cellulite may be painful depending on where it is located and how much fat is present. In such instances an improvement in appearance may be viewed as a reduction in stage based on the scale, i.e. going from stage 2 to stage 1.

Cellulite tends to accumulate on certain body regions, e.g., on the thighs and buttocks of many women, as well as on the abdomen, hip and/or upper arm region. In some embodiments, the extent of the area affected by cellulite is reduced, such that smaller areas of the thigh, buttocks, abdomen, hip, and/or upper arm region remain visibly affected. In certain embodiments, one of more such regions becomes free of visible signs of cellulite following treatment with a composition described herein.

In some embodiments, a method is provided for reducing the re-occurrence of cellulite in an area that was previously affected by cellulite, but showing little or no signs of cellulite currently. Reducing the re-occurrence refers to delaying the recurrence of any cellulite on a previously-affected area, or reducing the extent of cellulite that re-appears on the area, such that any recurrent cellulite is less noticeable than previous amounts.

A stronger dermal structure reduces the likelihood of fat nodules "blebbing" between connective tissue fibers or septa, which is believed to lead to the characteristic unsightly appearance of cellulite. Further, lower levels of subcutaneous fat further reduce the likelihood of such blebbing. As cellulite is believed to result from a combination of enlarged fat tissue and weak dermal structure, combating cellulite through these multiple approaches, as described herein, can provide superior results compared with products that utilize only one approach.

Anti-Obesity Benefits

In some embodiments, a method is provided for reducing obesity. The method can comprise topically applying to an area affected by unwanted fat deposition an effective amount of a *Melicope* extract in a cosmetically acceptable vehicle, for a length of time sufficient to reduce the unwanted fat. The extract can reduce fat accumulation and/or adipocyte differentiation, as described herein, to reduce weight, such as in targeted areas. Such areas may be "problem areas" from which the consumer finds it difficult to lose weight by general dieting and/or exercise, i.e., the hips, thighs, midriff, "love handles," etc.

In other embodiments, the *Melicope* extract may be administered orally in an appropriate formulation in order to address excess subcutaneous lipid over-production on a systemic level. In such embodiments, the extract may be administered with or without food and may be administered in conjunction with other known pharmaceuticals, supplements, or food additives known to maintain or reduce body weight.

Other approaches for treating obesity have been described and may be used with the *Melicope* extract, disclosed herein. See, e.g., WO 04/047746.

The composition will typically be applied to the skin one, two, or three times daily for as long as is necessary to achieve desired anti-lipid results. The treatment regimen may comprise daily application for at least one week, at least two weeks, at least four weeks, at least eight weeks, or at least twelve weeks. Chronic treatment regimens are also contemplated.

In a specific embodiment, the *Melicope* extract is provided in a pharmaceutically, physiologically, cosmetically, and dermatologically-acceptable vehicle, diluent, or carrier, where the composition is topically applied to an affected area of skin and left to remain on the affected area in an amount effective for improving the condition and aesthetic appearance of skin.

The method of the invention may be employed prophylactically to forestall lipid over-production including in patients that have not manifested signs of lipid over-production, most commonly in individuals between the ages of 20 to 35 years of age. The method may also reverse or treat signs of lipid over-production once manifested as is common in patients experiencing puberty and/or those over 35 years of age.

EXAMPLES

Example 1

A. Preparation of *Melicope* Extracts

The process generally follows a combination of steam distillation and hydro-distillation, as it uses partial immersion of the biomass and boiling water steam, although it is typically referred to as steam distillation. Steam distillation relies on heat to open the oil glands in the plant and the essential oil and water to mix. Then the increase in vapor pressure and corresponding reduction in boiling point which occurs with the mixing of 2 immiscible liquids allows the essential oil, which would normally have a boiling point of greater than 200° C., to boil at less than 100° C.

Leaves and terminal branchlets were cut from stands of *Melicope* growing wild on the north coast of New South Wales (NSW), Australia. Approximately 2.102 Kg of leaf biomass was loaded loosely into a 20 liter reaction vessel set up as a distillation unit with a receiver condenser and a 500 ml separating flask. 4 liters of hot water were added to the vessel and additional heat added via a hot plate. The flow rate of the condenser water was adjusted to give a distillate temperature of at least 50° C. in the separating funnel. The essential oil floated on the water. At approximately 1 hour intervals the water was drained off and returned to the vessel. The distillation was stopped after 8.5 hours when no further oil was distilled. The water in the separating flask was drained and the essential oil tapped off. The 2.102 Kg of leaf biomass produced 3.35 g of essential oil, a yield of 0.16%. The essential oil was found to have a relative density at 20° C. of 0.950 and a Refractive Index of 1.510 at 20° C.

As noted in the remaining specification, modifications and adaptations of this extraction process are possible, particularly during a scale-up to larger volumes for production.

B. Essential Oil Profile of *Melicope* Extracts

The essential oil content of the *Melicope* extracts were identified using the procedures detailed within Brophy et al. disclosed above and are reported below as weight percentages for each of the extracts.

TABLE 1

Essential Oil Profiles for *Melicope* Extracts

| Melicope Batch | Caryophyllene | Bicyclo-germacrene | Zierone | Evodone |
|---|---|---|---|---|
| Extract 1 | 5.7 | 0.9 | 28 | 14.1 |
| Extract 2 | 5.7 | 0.9 | 26.8 | 14.5 |
| Extract 3 | 4.4 | 0.9 | 27.2 | 12.8 |
| Extract 4 | 4.5 | 0.9 | 29.1 | 11.8 |
| Extract 5 | 4.9 | 1 | 27.8 | 13.5 |
| Extract 6 | 5.3 | 0.9 | 27.4 | 13.3 |

Example 2

Assay for Gene Expression of FAS, PPARγ, and SCD-1

Primary human preadipocytes were plated confluent in preadipocyte medium. Next day differentiation was initiated by adding adipocyte differentiation medium and cells were allowed to differentiate for 7 days. On the day 7 of differentiation, 1 volume of differentiation medium was left and 3 volumes of adipocyte maintenance medium were added. Cells were incubated for 7 days (14 days of differentiation total) and treated with 0.005% *Melicope* extract on days 8, 10, and 13 of differentiation. Day 10 and 13 treatment was added in adipocyte maintenance medium. After treatment, cells were washed with ice cold PBS, collected into RLT lysis buffer and RNA was extracted using RNeasy Mini Kit (Qiagen, Valencia, Calif.) following manufactures recommendations. 200 ng of RNA was used for cDNA synthesis using High Capacity cDNA Reverse Transcription Kit (Life Technologies, Carlsbad, Calif.). 1 uL of undiluted cDNA was used per qPCR reaction. Primers used for detection of septum protein mRNA were purchased from Life technologies (Carlsbad, Calif.). Following primers were used: PPARγ (cat# Hs0111511_m1), SCD-1 (cat# Hs01682761_m1), FAS (cat# Hs00163653_m1). Expression of septum protein mRNA was normalized to 18S rRNA. The conditions of q-PCR were: an incubation step at 50° C. for 2 minutes and an enzyme activation step at 95° C. for 10 minutes; followed by 45 cycles of 95° C. for 30 seconds and 60° C. for 1 minute. CT value was obtained from the software of the Stratagene MX2005P.

TABLE 2

Effect of 0.005% *Melicope* extract on gene expression in adipocytes

| Gene | % change over control | p value |
|---|---|---|
| FAS | −43.698 | 0.00351 |
| PPARγ | −71.1362 | 0.00008 |
| SCD-1 | −90.4462 | 0.00000 |

Example 3

Assay for Quantification of Intracellular Triglyceride Inhibition

Cryopreserved human primary pre-adipocytes harvested from the subcutaneous adipose tissue of a healthy female were obtained from Zen-Bio (Research Triangle Park, N.C.). Following the manufacturer's instructions, the pre-adipocytes were cultured in Pre-adipocyte Medium containing DMEM/Ham's F-12 (1:1, v/v), HEPES (pH 7.4), fetal bovine serum, penicillin, streptomycin, and amphotericin B (Zen-Bio), in a humidified 37° C. incubator with 5% $CO_2$. After reaching 90% confluence, the pre-adipocytes were allowed to differentiate into adipocytes by adding Adipocyte Differentiation Medium containing DMEM/Ham's F-12 (1:1, v/v), HEPES pH 7.4, fetal bovine serum, biotin pantothenate, human insulin, dexamethasone, isobutylmethylxanthine, penicillin, streptomycin, and amphotericin B (Zen-Bio).

Melicope extract was dissolved in ethanol and then added into cell culture for 7 days. Untreated adipocytes were used as a control. After 7 days of incubation, Adipocytes Differentiation Medium was replaced with Maintenance Medium, DMEM/Ham's F-12 (1:1, v/v), HEPES pH 7.4, fetal bovine serum, biotin pantothenate, human insulin, dexamethasone, penicillin, streptomycin, and amphotericin B, and the adipocytes continued under incubation for another 7 days. The production of triglycerides in the adipocytes was determined by using a triglyceride assay kit (Zen-Bio). Briefly, adipocytes were rinsed with a wash buffer and lysed in a lysis buffer following medium removal. Intracellular triglycerides were released into the lysis buffer and converted into glycerol-1-phosphate, which was subsequently oxidized to di-hydroxyacetone phosphate and hydrogen peroxide. Hydrogen peroxide was reacted with 4-aminoantipyrine (4-AAP) and sodium N-ethyl-N-(3-sulfopropyl)-m-anisidine (ESPA) to generate a quinoneimine dye, which shows an absorbance maximum at 540 nm. The increase in absorbance at 540 nm was directly proportional to the intracellular levels of triglycerides in the adipocytes. Results were obtained in triplicate and a p-value was determined.

TABLE 3

Effect of Melicope extract on lipid accumulation

| Concentration | % reduction of lipid accumulation | p value |
|---|---|---|
| 0.02% | −49.9% | 0.00 |

As shown in the table above, the Melicope extract exhibited nearly a 50% reduction in lipid accumulation within the adipocytes.

Example 4

Visualization of Lipid Accumulation

A. Cryopreserved human primary pre-adipocytes harvested from the subcutaneous adipose tissue of a healthy female were obtained from Zen-Bio (Research Triangle Park, N.C.). Following the manufacturer's instructions, the pre-adipocytes were cultured in Preadipocyte Medium containing DMEM/Ham's F-12 (1:1, v/v), HEPES (pH 7.4), fetal bovine serum, penicillin, streptomycin, and amphotericin B (Zen-Bio), in a humidified 37° C. incubator with 5% $CO_2$. After reaching 90% confluence, the pre-adipocytes were allowed to differentiate into adipocytes by adding Adipocyte Differentiation Medium containing DMEM/Ham's F-12 (1:1, v/v), HEPES pH 7.4, fetal bovine serum, biotin pantothenate, human insulin, dexamethasone, isobutylmethylxanthine, penicillin, streptomycin, and amphotericin B (Zen-Bio) and cells were differentiated following manufacturer's recommendation. After 7 days of incubation, Adipocytes Differentiation Medium were replaced with Maintenance Medium, DMEM/Ham's F-12 (1:1, v/v), HEPES pH 7.4, fetal bovine serum, biotin pantothenate, human insulin, dexamethasone, penicillin, streptomycin, and amphotericin B and maintenance media was used for the remaining time of incubation. Melicope extract was dissolved in ethanol and then added to adipocytes at 0.005% concentration 16 days after initiation of differentiation and replaced with fresh treatment on day 20 and 22. Untreated adipocytes were used as a control. To visualize the effect of Melicope extract on lipid accumulation, the same region cell culture dish was imaged under a light microscope on day 16 (prior to treatment) day 20 and day 23. Significant inhibition of lipid accumulation was observed. Alternatively, after treatment, triglyceride accumulation in lipid droplets was visualized by Oil Red-O staining (ICN Biomedicals Inc; Aurora, Ohio). The control and treated cells were each stained using the same procedure. After fixation with methanol-free formaldehyde, cells were incubated in Oil Red-O solution for 1 h at room temperature, washed with PBS, and imaged under light microscope. A comparison of the two images shows a substantial reduction in lipid accumulation within the cells treated with Melicope extract.

B. Visualization of Extended Benefits. Cryopreserved human primary pre-adipocytes harvested from the subcutaneous adipose tissue of a healthy female were obtained from Zen-Bio (Research Triangle Park, N.C.). Following the manufacturer's instructions, the pre-adipocytes ware cultured in Preadipocyte Medium containing DMEM/Ham's F-12 (1:1, v/v), HEPES (pH 7.4), fetal bovine serum, penicillin, streptomycin, and amphotericin B (Zen-Bio), in a humidified 37° C. incubator with 5% $CO_2$. After reaching 90% confluence, the pre-adipocytes were allowed to differentiate into adipocytes by adding Adipocyte Differentiation Medium containing DMEM/Ham's F-12 (1:1, v/v), HEPES pH 7.4, fetal bovine serum, biotin pantothenate, human insulin, dexamethasone, isobutylmethylxanthine, penicillin, streptomycin, and amphotericin B (Zen-Bio) and cells were differentiated following manufacturer's recommendation. After 7 days of incubation, Adipocytes Differentiation Medium were replaced with Maintenance Medium, DMEM/Ham's F-12 (1:1, v/v), HEPES pH 7.4, fetal bovine serum, biotin pantothenate, human insulin, dexamethasone, penicillin, streptomycin, and amphotericin B and maintenance media was used for the remaining time of incubation. Melicope extract was dissolved in ethanol (0.005% Melicope extract) and then added to adipocytes 16 days after initiation of differentiation. On day 20, 96 hours following treatment, the treatment was removed by washing the cells and replacing the medium with maintenance medium free of Melicope extract. Untreated adipocytes were used as a control. To visualize the effect of Melicope extract on lipid accumulation, the same region cell culture dish was imaged under light microscope on day 16 (prior to treatment), day 20 and day 23. As expected the day 20 image showed a substantial reduction in lipid accumulation, however, quite unexpectedly, the day 23 image showed that the substantial reduction in lipid accumulation was maintained 72 hours after withdrawal of the treatment on day 20.

Example 5

A. Exemplary Anti-Cellulite Compositions

Cosmetic compositions comprising an extract of *Melicope* for topical application to skin exhibiting or at risk of exhibiting cellulite are provided in Table 4.

TABLE 4

Sample Anti-Cellulite Cosmetic Composition
Ingredient

Aesthetic modifier
Emollient
Emulsifier
Anti-inflammation agent
Chelater
Coolant
Elastin stimulator
Exfoliator
Fragrance
Humectant
Microcirculation enhancer
Neutralizer
Preservative
Sunscreen
Collagenase/elastinase inhibitor
Hawthorne (*Crataeg. monog.*) Fruit. Extract
Coffee Seed Extract
Soybean (*Glycine soja*) Extract
*Celosia cristata* Extract & *Prunella vulgaris* Extract
L-Carnitine Hydrochloride
*Averrhoa carambola* Leaf Extract
*Melicope* extract
Demineralized water

B. Exemplary Anti-Sebum Composition

Cosmetic compositions comprising an extract of *Melicope* for topical application to skin exhibiting an over-production of sebum are provided in Table 5.

TABLE 5

Sample Anti-Sebum Facial Cosmetic Composition
Ingredient

Aesthetic modifier
Emollient
Emulsifier
Anti-inflammation agent
Chelater
Coolant
Elastin stimulator
Exfoliator
Fragrance
Humectant
Microcirculation enhancer
Neutralizer
Preservative
Sunscreen
Collagenase/elastinase inhibitor
Phytol
Antioxidant
Fennel Extract
Carrot extract
Pomegranate extract
Thiodipropionic acid (TDPA)
Green tea polyphenol
L-4 Thiazolylanine
*Melicope* extract
Demineralized water

C. Exemplary Skin Lightening Composition

Cosmetic compositions comprising an extract of *Melicope* for topical application to skin exhibiting signs of hyperpigmentation are provided in Table 6.

TABLE 6

Sample Skin Lightening Compositions
Description

Demineralized Water
Carbopol 934
Acrylates/C10-30 Alkyl Acrylate Crosspolymer
Acrylates/C10-30 Alkyl Acrylate Crosspolymer
Xanthan Gum
Disodium EDTA - Tech Grade
Methylparaben
Alcohol SD40B
Alcohol Mixture (3210&1901 92.52-7.48)
Alcohol Mixture (3215&1901 92.52-7.48)
Phenoxyethanol-98% MIN (*RI*)
Butylene Glycol
Pentylene Glycol (*RI*)
Ethoxydiglycol
ISODODECANE
Dilauryl Thiodipropionate
Tetrahexyldecyl Ascorbate
Ascorbyl Glucoside
Glycyrrhizinate - *Dipotassium* Unp.
Silica Shells
Sodium Hydroxide Solution 50%
Silicone Fluid SF-96-5
PEG-40 Stearate
Steareth-2
*Saxifraga Sarmentosa*/Grape Extract
*Saccharomyces*/Zinc ferment
Yeast Extract
Kudzu (*Pueraria Lobata*) Symbiosome extract
Soybean (*Gly. Soja*) Extract
Carrot (*Daucus Carota Sativa*) Root Extract
Phytol
Dimethicone/Dimethicone Crosspolymer
Thiodipropionic Acid
*Melicope* Extract These compositions are believed to be effective to treat, reverse, ameliorate and/or prevent signs of the presence and/or production of excess lipids, specifically, the compositions are believed to reduce the appearance of cellulite and/or subcutaneous fat in the skin, and excess sebum, respectively. The compositions of Tables 4-6 are applied to skin in need of treatment, by which is meant skin in need of an anti-cellulite or anti-sebum benefit, respectively. The cosmetic compositions may be applied directly to the skin in need of treatment. The exemplary anti-cellulite compositions may be applied to treat, reverse, ameliorate and/or prevent cellulite on any surface of the skin, including without limitation, the skin of the thighs, abdomen, buttocks, and/or appendages (arms or legs). The exemplary anti-sebum composition may be applied to treat, reverse, ameliorate, and/or prevent the effects of excess sebum production on any surface of the skin, including without limitation, the skin, including hair and scalp, neck, shoulders, back and chest.

These cosmetic compositions are applied to the skin, cellulite and/or areas exhibiting excess subcutaneous fat, two or three times daily for as long as is necessary to achieve desired anti-lipid results, a treatment regimen which may comprise daily application for at least one week, at least two weeks, at least four weeks, at least eight weeks, or at least twelve weeks. Alternatively, the exemplary cosmetic compositions may be used in chronic treatment of the skin, cellulite and/or excess subcutaneous fat.

Example 6

Prophetic Example of In Vivo Protocol of Sebum Test

Reference: J Invest Dermatol. 2003 June; 120(6):915-22

Healthy subjects will be selected based on inclusive and exclusive criteria. The participants will not be allowed to apply creams and ointments on the face 2 weeks prior to and during the time of the study. Topical formula containing actives may be applied onto the skin surface of forehead for a period of time before skin surface lipid is collected from subjects. Samples of sebum may be collected from the forehead of the subjects using Sebutapes® (Cuderm, Dallas, Tex.). Briefly, forehead skin will be cleaned prior to sample acquisition using a sterile gauze ball (Gazin®, Lohmann & Rauscher International GmbH, Rengsdorf, Germany) soaked in 1 ml 70% ethanol solution. Each tape will be weighed before and after sebum collection to determine the amount of sebum collected. The sebum collection time will be 1 h for every tape. Immediately after collection and weighing, sebum-enriched tapes will be irradiated with defined doses of UVB and UVA and, subsequently, stored in Eppendorf tubes at −80° C. until further use. Sebum-enriched Sebutapes® will be extracted in 1 ml HPLC grade ethanol by vortexing for 1 min in 1.5 ml Eppendorf tubes. Then, tapes will be removed and the remainder will be centrifuged at 2920×g and 4° C. for 10 min 750 μl of each supernatant will be transferred into an Eppendorf tube and directly subjected to HPLC analysis.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A method for treating human skin experiencing lipid over-production comprising topically applying to skin in need thereof a composition comprising an effective amount of *Melicope elleryana* extract in a cosmetically acceptable vehicle.

2. The method of claim 1, wherein said skin benefit is selected from the group consisting of:
   (a.) reducing lipid production by sebaceous glands;
   (b.) reducing lipid synthesis in subcutaneous adipose tissue;
   (c.) reducing triglyceride synthesis;
   (d.) reducing fatty acid synthesis;
   (e.) preventing and/or improving conditions related to skin associated with inhibited lipolysis;
   (f.) preventing and/or improving conditions related to skin associated with nonselective or partially selective PPAR-γ stimulators/up regulators;
   (g.) preventing and/or improving conditions related to skin associated with nonselective or partially selective up regulation of adipogeneic genes typically up regulated by PPAR-γ activation;
   (h.) preventing and/or improving conditions related to skin associated with nonselective or partially selective FAS stimulators/up regulators;
   (i.) preventing and/or improving conditions related to skin associated with nonselective or partially selective SCD-1 stimulators/up regulators;
   (j.) preventing, ameliorating or treating oily skin;
   (k.) preventing, ameliorating or treating oily hair;
   (l.) preventing, ameliorating or treating oily scalp;
   (m.) preventing, ameliorating or treating enlarged pores;
   (n.) preventing, ameliorating, or treating acne-prone skin;
   (o.) preventing, ameliorating or treating body odors associated with excess sebum production;
   (p.) preventing, ameliorating or treating cellulite in adults;
   (q.) preventing, ameliorating or treating excess accumulation or production of subcutaneous fat in adults;
   (r.) improving skin texture associated with cellulite; and combinations thereof.

3. The method of claim 1, wherein the skin in need thereof is skin having excess sebum.

4. The method of claim 3, wherein the human skin is located on a human's back, shoulders, neck, scalp, hair or face.

5. The method of claim 4, wherein the human skin is located on a human's face.

6. The method of claim 3, wherein the skin benefit is selected from the group consisting of:
   a. restoration of a matte finish to the skin;
   b. an evening of skin type;
   c. reduction in oily/greasy feel to skin and/or hair;
   d. reduction in the incidence of dandruff;
   e. reduction in the incidence of blocked/clogged pores;
   f. reduction in the incidence of comedones;
   g. reduction in the incidence of acne lesions;
   h. reduction in the area over expressing or over-producing lipids;
   i. reduction in thickness of skin affected by over-production of lipids; and combinations thereof.

7. The method of claim 1, wherein the skin in need thereof is skin having cellulite.

8. The method according to claim 7, wherein said cellulite is found on a thigh, buttocks, abdomen, hip, and/or upper arm region.

9. The method according to claim 7, wherein said skin benefit is selected from the group consisting of:
   (a) reduction in the appearance of cellulite lumpiness and/or unevenness;
   (b) reduction in pitting appearance of cellulite upon squeezing;
   (c) reduction in the extent of area affected by cellulite;
   (d) prevention or delay in the recurrence of cellulite;
   (e) improvement in adipocyte/fat tissue disposition; and combinations thereof.

10. The method according to claim 1, wherein the skin in need thereof is skin with excess subcutaneous fat.

11. The method according to claim 1, wherein the *Melicope* extract is an essential oil.

12. The method of claim 11, wherein the essential oil comprises caryophylene, bicyclogermacrene, zierone, and evodone.

13. The method according to claim 1, of wherein the *Melicope* extract is used in combination with at least one other anti-lipid agent.

14. The method according to claim 13, wherein said at least one other anti-lipid agent comprises a carnitine palmitoyl transferase-1 stimulator.

15. The method of claim 1, wherein the modulator is in combination with at least one anti-cellulite agent.

16. The method of claim 15, wherein the at least one anti-cellulite agent is selected from the group consisting of a phophodiesterase inhibitor, an adenylate cyclase activator, a lipolysis stimulator, a beta-adrenergic receptor agonist, an alpha-2-adreneric receptor antagonist, *perilla* oil, carnitine, creatine, and combinations thereof.

17. The method of claim 16, wherein said at least one other anti-cellulite agent further comprises at least one agent selected from the group consisting of a xanthine analog, forskolin, a *Coleus forskohlii* extract, a hawthorne extract, a cola extract, isoproterenol, yohimbine, *Ginkgo biloba* extract, and *perilla* oil.

18. The method of claim 17, wherein said at least one other anti-cellulite agent is caffeine.

19. The method according to claim 1, wherein the *Melicope* extract is used in combination with at least one collagen and/or elastin stimulator.

20. The method of claim 1, wherein said composition is applied at least once daily.

21. The method of claim 1, wherein an effective amount of the *Melicope* extract is about 0.001% to about 25% by weight.

22. The method of claim 21, wherein the *Melicope* extract is present in an amount from about 0.001% to about 1% by weight.

23. The method of claim 1, wherein said composition is a leave-on composition.

24. The method of claim 1, wherein said topical application comprises daily application for a period of at least 4 weeks.

25. The method according to claim 1, wherein the cosmetically acceptable vehicle is a transdermal patch.

26. The method according to claim 1, wherein the cosmetically acceptable vehicle is an emulsion.

27. A method for treating human skin experiencing lipid over-production comprising administering to an individual in need thereof an oral composition comprising an effective amount of *Melicope elleryana* extract in an acceptable vehicle.

\* \* \* \* \*